(12) United States Patent
Cumming

(10) Patent No.: US 6,497,708 B1
(45) Date of Patent: Dec. 24, 2002

(54) INTRAOCULAR LENS INSERTION INSTRUMENT

(75) Inventor: J. Stuart Cumming, Anaheim, CA (US)

(73) Assignee: Medevec Licensing, B.V. (NL)

( * ) Notice: Subject to any disclaimer, the term of this patent is extended or adjusted under 35 U.S.C. 154(b) by 0 days.

(21) Appl. No.: 09/075,931

(22) Filed: May 11, 1998

(51) Int. Cl.[7] .................................................. A61F 9/00
(52) U.S. Cl. ...................................... 606/107; 623/6.12
(58) Field of Search ...................... 606/107; 623/4–6, 623/4.1, 6.11, 6.12, 6.43–6.62

(56) References Cited

U.S. PATENT DOCUMENTS

| | | |
|---|---|---|
| 4,573,998 A | 3/1986 | Mazzocco |
| 4,681,102 A | 7/1987 | Bartell |
| 4,715,373 A | 12/1987 | Mazzocco et al. |
| 4,976,716 A | 12/1990 | Cumming |
| 5,275,604 A * | 1/1994 | Rheinish et al. ............ 606/107 |
| 5,304,182 A * | 4/1994 | Rheinish et al. ............ 606/107 |
| 5,324,306 A * | 6/1994 | Makower et al. ........... 606/213 |
| 5,425,734 A * | 6/1995 | Blake ......................... 606/107 |
| 5,474,562 A * | 12/1995 | Orchowski et al. ......... 606/107 |
| 5,873,879 A * | 2/1999 | Figueroa et al. ............ 606/107 |
| 5,944,725 A * | 8/1999 | Cicenas et al. ............. 606/107 |

* cited by examiner

*Primary Examiner*—Glenn K. Dawson
(74) *Attorney, Agent, or Firm*—Boniard I. Brown

(57) ABSTRACT

An insertion instrument provides improved features for insertion of a lens into the eye through a small incision. A tubular member has a lumen and a split nozzle end portion for spreading after insertion. Ridges on the lumen wall prevent rotation of the lens, and stabilizer components extend from a plunger end portion to maintain the lens compressed and to prevent lens rotation in moving through the lumen.

14 Claims, 3 Drawing Sheets

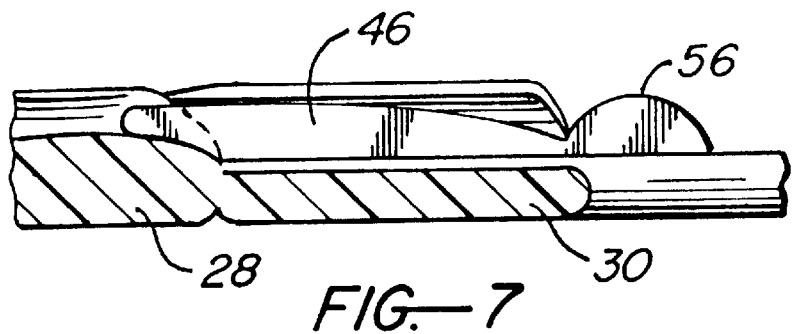
FIG.—7
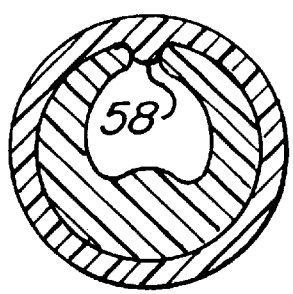
FIG.—8
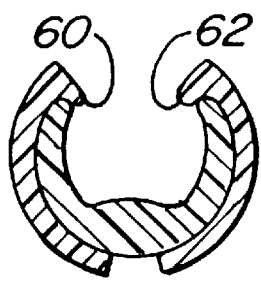
FIG.—9
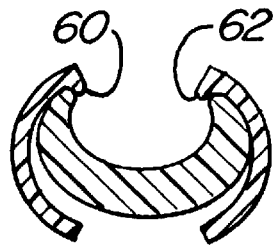
FIG.—10
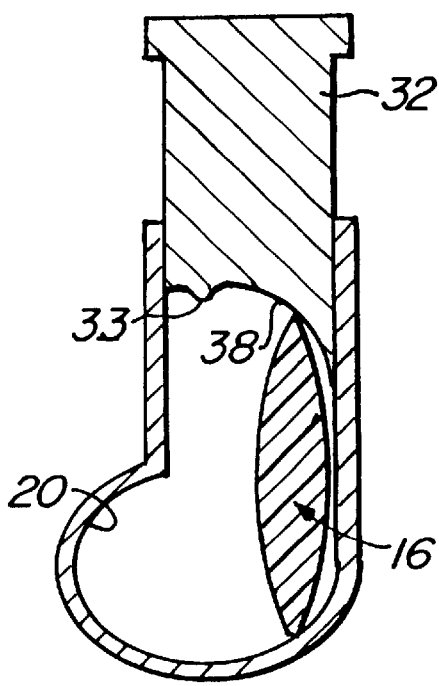
FIG.—11A
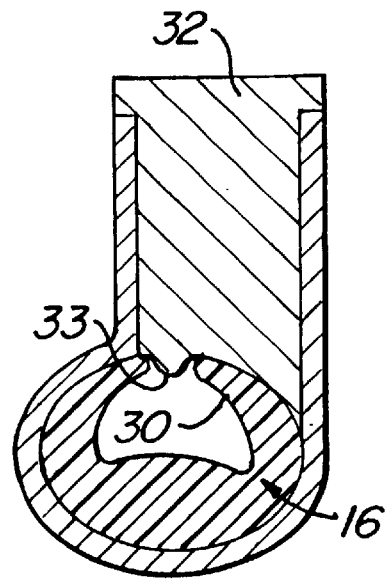
FIG.—11B

INTRAOCULAR LENS INSERTION INSTRUMENT

RELATED APPLICATION

The present application is related to Applicant's pending application Ser. No. 08/751,181 which shows and describes some related features.

BACKGROUND AND SUMMARY OF THE INVENTION

The present invention addresses problems related to the insertion of an intraocular lens through a small incision in the human eye.

Reference is made to Applicant's related application Ser. No. 08/751,181, wherein are illustrated and described certain relevant features and components, which application is incorporated herein by reference.

In recent years, foldable intraocular lenses have largely replaced hard, rigid lenses, the foldable lens being insertable through an incision of approximately ½ the size of an incision required for rigid lenses. A small incision enables more rapid recovery, less discomfort for a patient, and avoids many of the possible adverse complications of cataract surgery. Further, the procedure requires less time because suturing is not required.

The problems addressed include undesirable rotation of a folded, compressed lens during passage through a lumen or tubular passage, the maintaining of the correct orientation of a lens relative to an insertion instrument, sudden expansion of unfolding of a compressed lens as it exits the insertion instrument into the eye, and difficulty in insertion of a tip of an insertion instrument into a small incision in the eye of a patient.

Although various folding forceps have been provided for folding flexible lenses, it has generally been preferred by surgeons to utilize insertion devices whereby a lens enters the eye through a tube. Folding forcep devices generally comprise two components in addition to a lens, thus requiring two hands for their utilization.

The improvements according to the invention include a plunger with stabilizing components thereon to exert forces on a folded lens to maintain the lens in folded configuration and to prevent rotation of the lens relative to a lumen wall.

One or more slits in the nozzle end portion enable the spreading of the end portion by passage therethrough of the folded lens after insertion in the eye of a patient, thus to provide ease of admission of the folded lens into the eye of a patient.

Ridges extend longitudinally of the lumen wall to aid in prevention of rotation of a folded lens relative to the lumen wall, these including ridges extending along opposite edges of at least one slit in the nozzle end portion of the insertion instrument to aid in the prevention of rotation of a folded lens relative to the lumen wall.

BRIEF DESCRIPTION OF THE DRAWINGS

FIG. 7 is an enlarged partial sectional view, taken at line 7—7 in FIG. 6;

FIGS. 8, 9 and 10 are sectional views taken at lines 8—8, 9—9, and 10—10 in FIG. 1, showing a folded lens in different configurations in the plunger at successive positions in moving through the lumen; and FIGS. 11A and 11B are sectional views showing the interrelationship among the ram, lumen and lens in the folding of the lens into folded configuration in a pre-insertion position in the lumen-tube.

DESCRIPTION OF THE PREFERRED EMBODIMENT

Figure 1:
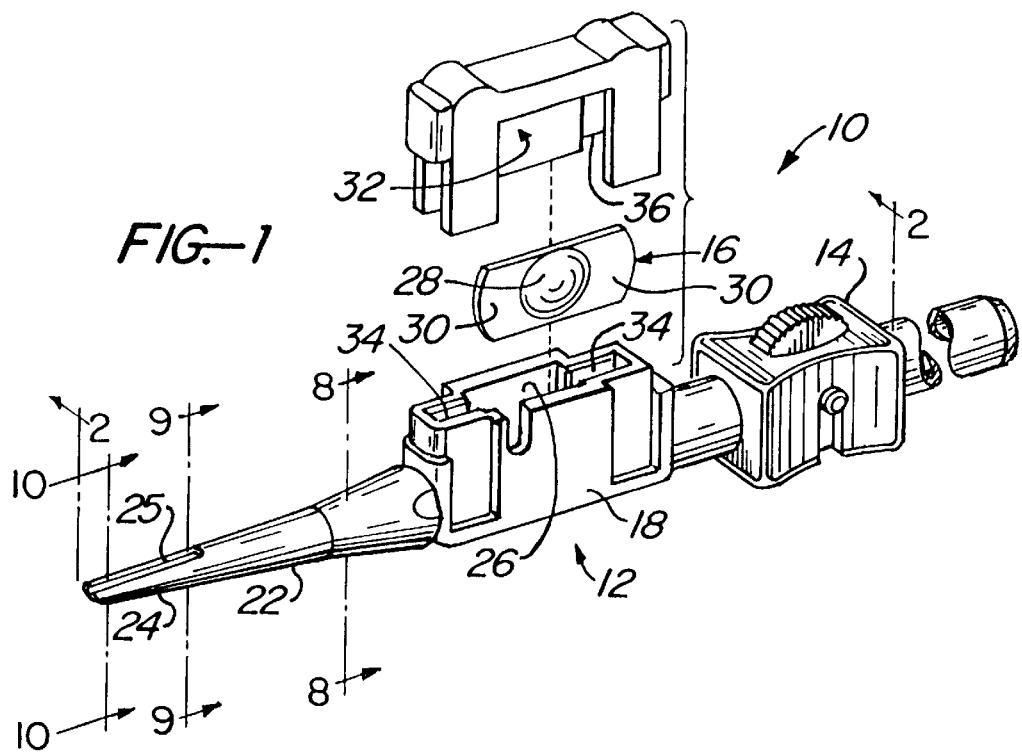
FIG. 1 is an exploded perspective view of an insertion instrument of the present invention showing its receptacle actuator, tubular portion and nozzle.
Figure 2:
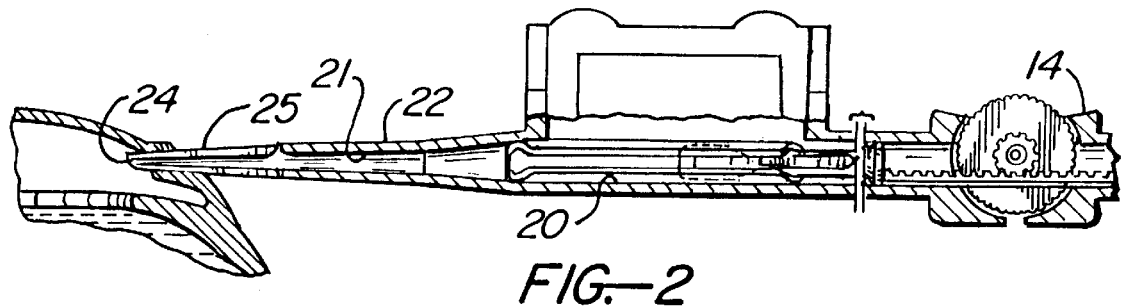
FIGS. 2 and 3 are sectional views of the instrument of FIG. 1, showing a lens optic and haptics in folded configuration in the lumen with the nozzle tip inserted through an incision in the eye of a patient.
Figure 3:
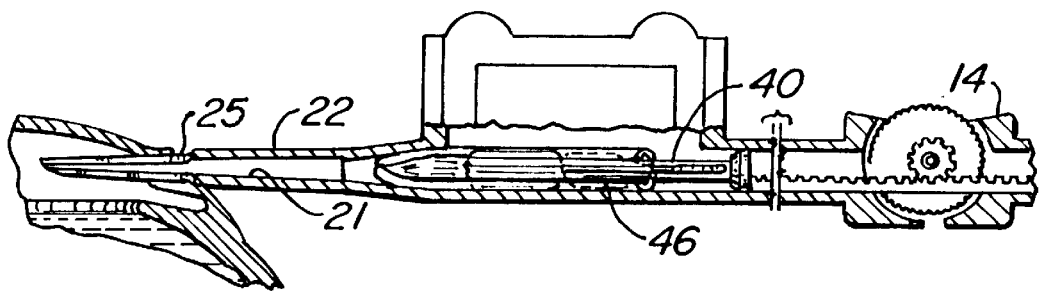
Figure 4:
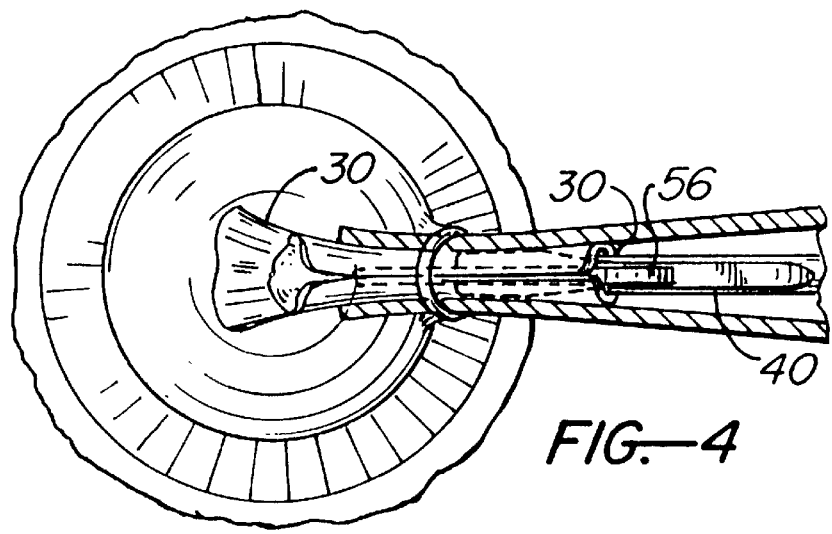
FIG. 4 is an enlarged fragmentary view of the nozzle portion, showing the nozzle tip portion inserted via an incision in the eye of the patient, and the lens expanding within the eye.

Referring to the drawings, there is shown an improved insertion instrument 10 for inserting an intraocular lens into a patient's eye via a small incision. The instrument generally includes a lens insertion assembly 12 and an insertion actuator 14. The lens insertion instrument is adapted to receive a foldable intraocular lens 16 in an unfolded configuration.

Figure 5:
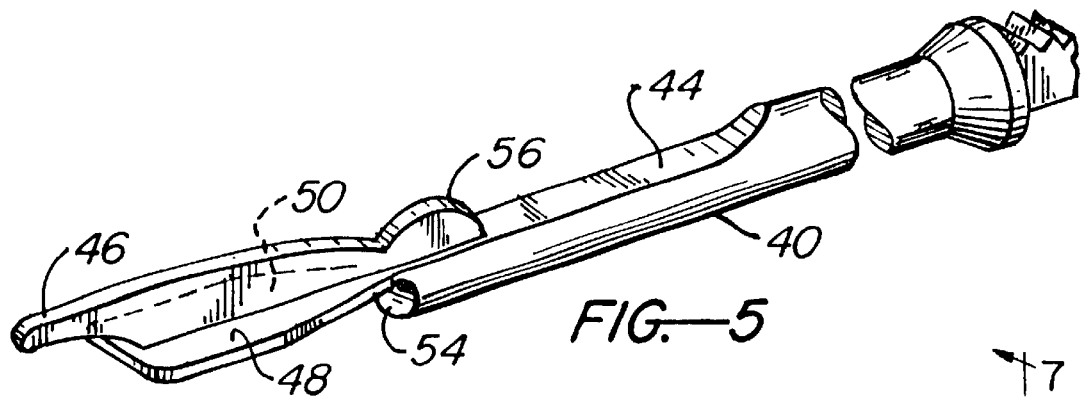
FIG. 5 is a perspective view of a plunger and stabilizer components thereon, according to the present invention.

As utilized herein for purposes of description, the terms "horizontal", "vertical", "upward" and "downward" are defined in relation to preferred orientation normally employed by a surgeon in using the instrument in the insertion of an intraocular lens into the eye of a patient. In this context, "horizontal" is a longitudinal direction of the instrument and plunger as indicated in FIGS. 1 and 5, and "vertical" is the direction perpendicular to such horizontal orientation. However, the insertion instrument may be utilized in other orientations.

The lens insertion assembly 10 includes a receptacle 18 and an elongate tubular portion 20 which has an interior passage or lumen 21, a nozzle 22, and a tip 24 for insertion into the eye, the nozzle having a longitudinal slit 25, as shown. The nozzle and tubular portion may typically be fabricated of polycarbonate, polyethylene, polystyrene, or other plastic with adequate flexibility.

The lumen or bore 21 extends axially through tubular portion 20, and has a longitudinal central axis. The receptacle 18 is preferably formed integrally with the tubular portion and has a lens storage chamber 26 extending laterally of the bore 24 through an opening (not shown) in the wall of the bore.

The foldable lens 16 is formed of appropriate flexible optical lens material, and has a central optic 28 and generally flat plate haptics 30 joined to opposite edges of the optic in a generally common plane transverse to the optic axis. Other types of foldable lenses may be utilized.

The lens storage chamber 26 receives the lens in its unfolded configuration. A ram 32 serves as lens transfer and folding means, and cooperates with the chamber and receptacle 18 to define the lens storage space. The ram is operable by the user to move the unfolded lens from this storage position into the lumen or bore 21 (FIG. 11A) via the opening in the bore wall, and to fold the lens into a compact folded configuration with the lens in a pre-insertion position in the bore or lumen (FIG. 11B).

The ram and receptacle have mating interfitting male and female configurations of slots 34 and ram wing portions 36.

Referring to FIGS. 11A and 11B, the inner end of the ram has an arcuate end face 38 across which extends a transverse ridge 33 which is aligned with the longitudinal axis of the bore or lumen 21. The inner curvature 38 of the ram is curved like the inner surface of the bore or lumen (FIG. 11B). The end surface or face 38 of the ram is flush with the inner wall surface of the lumen and faces the opposing wall surface of the bore.

Figure 6:
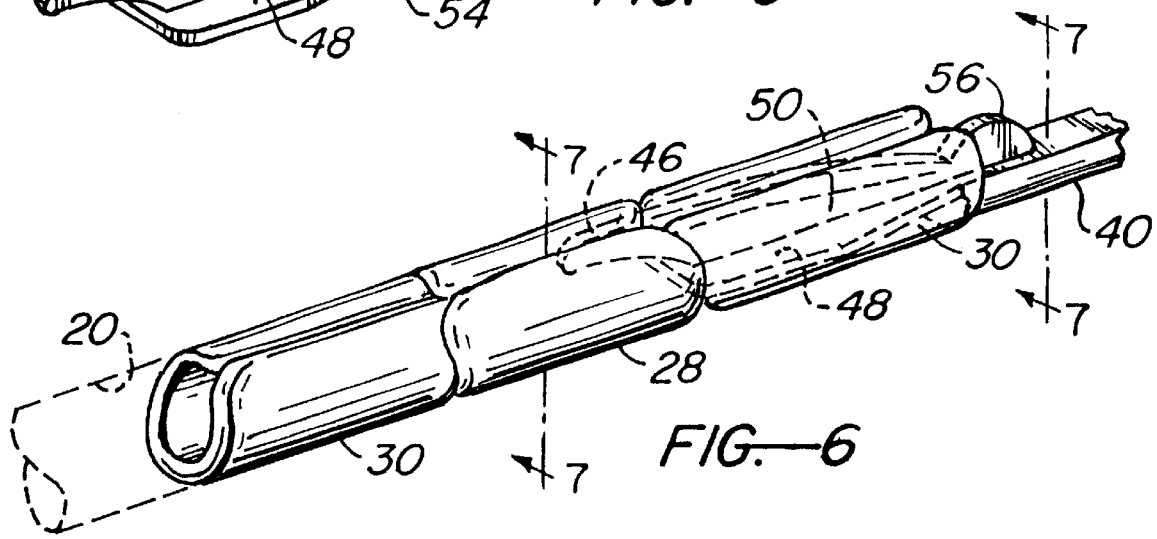
FIG. 6 is a perspective cutaway view of the plunger and stabilizers thereof in relation to a folded lens optic and haptics in the lumen of the instrument of FIGS. 2 and 3.

A plunger 40 (FIG. 5) constitutes a lens insertion device for moving the folded lens 28, 30 (FIG. 6) through the lumen and the nozzle tip 24 to urge the lens through the tip and into the eye of the patient. The lens is wrapped about the end portion of the plunger as it moves through the lumen, as indicated in FIG. 6.

A reduced, flat portion 44 of the plunger has extending therefrom a generally vertical stabilizer 46 and a horizontal stabilizer having oppositely extending wing portions 48, 50, as shown. A generally vertical reinforcing rib 56 extends from the vertical stabilizer 46 to provide rigidity. The end portion 54 of the plunger is recessed and concave, thus to better engage the end portion of a folded lens for accurately urging of the lens through the lumen.

Manual operation of insertion actuator 14, which is preferably a rack and pinion arrangement, as shown, causes the end of plunger 40 to engage the lens in its pre-insertion position, and to urge the lens along the lumen toward nozzle 22 and tip 24, and thence into the eye of the patient.

A longitudinal ridge 58 is defined on the lumen wall (FIG. 8) and is aligned with ridge 33 on the inner ram surface to prevent rotation of the lens relative to the lumen wall.

Ridges 60, 62 are defined at opposite edges of slit wall. These ridges retain the lens against rotation relative to the lumen wall during movement along the lumen.

In moving through the lumen and nozzle, the folded lens has the successive configurations indicated in FIGS. 8, 9 and 10, the lens being gradually opened to the configuration of FIG. 10.

In passing through the nozzle and the outlet or tip 24, the slitted end portions of the nozzle and tip are spread open, the spreading being limited by the size of the incision in the eye.

Thus there has been shown and described an intraocular lens insertion instrument which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

What is claimed is:

1. An insertion instrument for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, and having a lens insertion opening spaced from said outlet end opening, a lens receptacle defining a lens chamber communicating with said lens insertion opening in said tubular member, said lens receptacle having oppositely laterally extending slot portions, a ram slidable in said lens chamber and having laterally oppositely extending wing portions slidable in said lens receptacle slot portions, said ram having an end portion contoured to cooperate with an inner lumen wall to fold the lens into a folded pre-insertion configuration, a plunger for urging the lens through said lumen and outwardly therefrom into the eye, and a ridge extending longitudinally on the lumen wall from said lens insertion opening in the direction of said nozzle portion for prevention of rotation of the folded lens relative to the lumen wall.

2. An insertion instrument according to claim 1, and further including:

ridges defined on the lumen wall and extending along opposite edges of at least one slit to retain the lens against rotation relative to the lumen wall during movement through the nozzle.

3. An insertion instrument for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, and having a lens insertion opening spaced from said outlet end opening, a lens receptacle defining a lens chamber communicating with said lens insertion opening in said tubular member, said lens receptacle having oppositely laterally extending slot portions, a ram slidable in said lens chamber and having laterally oppositely extending wing portions slidable in said lens receptacle slot portions, said ram having an end portion contoured to cooperate with an inner lumen wall to fold the lens into a folded pre-insertion configuration, a plunger for urging the lens through said lumen and outwardly therefrom into the eye, and a ridge on said end portion of the ram and aligned with a ridge extending longitudinally on the lumen wall, said ridge on the ram end portion being positioned and adapted to retain the folded lens against rotation relative to said inner lumen wall.

4. An insertion instrument according to claim 3, and further including:

ridges defined on the lumen wall and extending along opposite edges of at least one slit to retain the lens against rotation relative to the lumen wall during movement through the nozzle.

5. An insertion apparatus for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, said tapered nozzle portion having defined therein at least one longitudinal slit extending to said outlet opening for resilient spreading of the tapered nozzle portion upon movement therethrough of the lens, ram means for insertion into the lumen of said lens via an insertion opening in the tubular member with said lens in a folded condition, a plunger for urging the lens through the lumen and outwardly therefrom into the eye, a ridge extending longitudinally on the lumen wall from the lens insertion opening and toward said nozzle portion to prevent rotation of the folded lens relative to the lumen wall during movement through the lumen, an optic stabilizer extending forwardly and upwardly of the forward end portion of the plunger to engage the folded optic of the lens to urge it downwardly and forwardly, and at least one plate stabilizer extending laterally outwardly from the forward end portion of the plunger to overlay and exert pressure on a lens haptic to aid in maintaining the haptic in folded configuration and properly oriented during movement through the lumen.

6. An insertion instrument for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, and having a lens insertion opening spaced from said outlet end opening, a lens receptacle defining a lens chamber communicating with said lens insertion opening in said tubular member, said lens receptacle having oppositely laterally extending slot portions, a ram slidable in said lens chamber and having laterally oppositely extending wing portions slidable in said lens receptacle slot portions, said ram having an end portion contoured to cooperate with an inner lumen wall to fold the lens into a folded pre-insertion configuration, a plunger for urging the lens through said lumen and outwardly therefrom into the eye, and ridges defined on the lumen wall and extending along opposite edges of at least one slit to retain the lens against rotation relative to the lumen wall during movement through the nozzle.

7. An insertion apparatus for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, said tapered nozzle portion having defined therein at least one longitudinal slit extending to said outlet opening for resilient spreading of the tapered nozzle portion upon movement therethrough of the lens, ram means for insertion into the lumen of said lens via an insertion opening in the tubular member with said lens in a folded condition, a plunger for urging the lens through the lumen and outwardly therefrom into the eye, ridges defined on the lumen wall and extending along opposite edges of the at least one slit to retain the lens against rotation relative to the lumen wall during movement through the nozzle, an optic stabilizer extending forwardly and upwardly of the forward end portion of the plunger to engage the folded optic of the lens to urge it downwardly and forwardly, and at least one plate stabilizer extending laterally outwardly from the forward end portion of the plunger to overlay and exert pressure on a lens haptic to aid in maintaining the haptic in folded configuration and properly oriented during movement through the lumen.

8. An insertion apparatus for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, said tapered nozzle portion having defined therein at least one longitudinal slit extending to said outlet opening for resilient spreading of the tapered nozzle portion upon movement therethrough of the lens, ram means for insertion into the lumen of said lens via an insertion opening in the tubular member with said lens in a folded condition, a plunger for urging the lens through the lumen and outwardly therefrom into the eye, a ridge extending longitudinally on the lumen wall from the lens insertion opening and toward said nozzle portion to prevent rotation of the folded lens relative to the lumen wall during movement through the lumen, ridges defined on the lumen wall and extending along opposite edges of the at least one slit to retain the lens against rotation relative to the lumen wall during movement through the nozzle, an optic stabilizer extending forwardly and upwardly of the forward end portion of the plunger to engage the folded optic of the lens to urge it downwardly and forwardly, and at least one plate stabilizer extending laterally outwardly from the forward end portion of the plunger to overlay and exert pressure on a lens haptic to aid in maintaining the haptic in folded configuration and properly oriented during movement through the lumen.

9. An insertion apparatus for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, said tapered nozzle portion having defined therein at least one longitudinal slit extending to said outlet opening for resilient spreading of the tapered nozzle portion upon movement therethrough of the lens, ram means for insertion into the lumen of said lens via an insertion opening in the tubular member with said lens in a folded condition, a plunger for urging the lens through the lumen and outwardly therefrom into the eye, a ridge extending longitudinally on the lumen wall from said lens insertion opening in the direction of said nozzle portion for prevention of rotation of the folded lens relative to said lumen defined by the tubular member, an optic stabilizer extending forwardly and upwardly of the forward end portion of the plunger to engage the folded optic of the lens to urge it downwardly and forwardly, and at least one plate stabilizer extending laterally outwardly from the forward end portion of the plunger to overlay and exert pressure on a lens haptic to aid in maintaining the haptic in folded configuration and properly oriented during movement through the lumen.

10. An insertion apparatus for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, ram means for insertion into the lumen of said lens via an insertion opening in the tubular member with said lens in a folded condition, plunger means for urging the lens through the lumen and outwardly therefrom into the eye, at least one stabilizer extending outwardly from a forward end portion of the plunger to exert force on the folded lens to maintain the lens in predetermined orientation and in folded configuration during movement of the lens through the lumen, said ram means comprises a ram member slidably mounted for movement through said insertion opening, said ram member has an end portion contoured to cooperate with an inner wall of said lumen to fold the lens into a folded pre-insertion configuration, and said contoured ram end portion having a curvature similar to a curvature of a confronting tubular member wall and extends to engage the lens to roll and fold the lens between the ram contoured end portion and the curved tubular member wall.

11. An insertion apparatus for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, said tapered nozzle portion having defined therein at least one longitudinal slit extending to said outlet opening for resilient spreading of the tapered nozzle portion upon movement therethrough of the lens, ram means for insertion into the lumen of said lens via an insertion opening in the tubular member with said lens in a folded condition, said ram means having an end portion contoured to cooperate with an inner lumen will to fold the lens into a folded pre-insertion configuration, said contoured ram end portion having a curvature similar to a curvature of a confronting tubular member wall and extending to engage the lens to roll and fold the lens between the ram contoured end portion and the curved tubular member wall, a lens receptacle defining a lens chamber communicating with said lens insertion opening in said tubular member, said ram means being slidable in said lens chamber, a plunger for urging the lens through the lumen and outwardly therefrom into the eye, an optic stabilizer extending forwardly and upwardly of the forward end portion of the plunger to engage the folded optic of the lens to urge it downwardly and forwardly, and at least one plate stabilizer extending laterally outwardly from the forward end portion of the plunger to overlay and exert pressure on a lens haptic to aid in maintaining the haptic in folded configuration and properly oriented during movement through the lumen.

12. An insertion instrument for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, and having a lens insertion opening spaced from said outlet end opening, a lens receptacle defining a lens chamber communicating with said lens insertion opening in said tubular member, said lens receptacle having oppositely laterally extending slot portions, a ram slidable in said lens chamber and having laterally oppositely extending wing portions slidable in said lens receptacle slot portions, said ram having an end portion contoured to cooperate with an inner lumen wall to fold the lens into a folded pre-insertion configuration, said contoured ram end portion having a curvature similar to a curvature of a confronting tubular member wall and extends to engage the lens to roll and fold the lens between the ram contoured end portion and the curved tubular member wall, a transverse ridge on the end portion of the ram disposed opposite and confronting the tubular member to retain lens end portions against relative movement relative to the ram, and a plunger for urging the lens through said lumen and outwardly therefrom into the eye.

13. An insertion apparatus for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, ram means for insertion into the lumen of said lens via an insertion opening in the tubular member with said lens in a folded condition, plunger means for urging the lens through the lumen and outwardly therefrom into the eye, at least one stabilizer extending outwardly from a forward end portion of the plunger means to exert force on the folded lens to maintain the lens in predetermined orientation and in folded configuration during movement of the lens through the lumen, said ram means comprising a ram member slidably mounted for movement through said insertion opening, said ram member having an end portion contoured to cooperate with an inner wall of said lumen to fold the lens into a folded pre-insertion configuration, said contoured ram end portion having a curvature similar to a curvature of a confronting tubular member wall and extends to engage the lens to roll and fold the lens between the ram contoured end portion and the curved tubular member wall, and a transverse ridge on the end portion of the ram member disposed opposite and confronting the tubular member to retain lens end portions against relative movement relative to the ram member.

14. An insertion apparatus for delivery of an intraocular lens into a human eye through a small incision, said apparatus including:

an elongate generally tubular member having a longitudinal axis and defining a lumen, said tubular member having a tapered nozzle portion defining an outlet end opening for release of the lens into the eye, said tapered nozzle portion having defined therein at least one longitudinal slit extending to said outlet opening for resilient spreading of the tapered nozzle portion upon movement therethrough of the lens, ram means for insertion into the lumen of said lens via an insertion opening in the tubular member with said lens in a folded condition, said ram means having an end portion contoured to cooperate with an inner lumen wall to fold the lens into a folded pre-insertion configuration, said contoured ram end portion having a curvature similar to a curvature of a confronting tubular member wall and extending to engage the lens to roll and fold the lens between the ram contoured end portion and the curved tubular member wall, a lens receptacle defining a lens chamber communicating with said lens insertion opening in said tubular member, said ram means being slidable in said lens chamber, a transverse ridge on the end portion of the ram means disposed opposite and confronting the tubular member to retain lens end portions against relative movement relative to the ram means, a plunger for urging the lens through the lumen and outwardly therefrom into the eye, an optic stabilizer extending forwardly and upwardly of the forward end portion of the plunger to engage the folded optic of the lens to urge it downwardly and forwardly, and at least one plate stabilizer extending laterally outwardly from the forward end portion of the plunger to overlay and exert pressure on a lens haptic to aid in maintaining the haptic in folded configuration and properly oriented during movement through the lumen.

* * * * *